United States Patent
Hernandez Altamirano et al.

(10) Patent No.: US 10,167,249 B2
(45) Date of Patent: Jan. 1, 2019

(54) AMINO AND IMINO PROPIONIC ACIDS, PROCESS OF PREPARATION AND USE

(71) Applicant: INSTITUTO MEXICANO DEL PETROLEO, Mexico City (MX)

(72) Inventors: Raul Hernandez Altamirano, Mexico City (MX); Luis Silvestre Zamudio Rivera, Mexico City (MX); Violeta Yasmin Mena Cervantes, Mexico City (MX); Hiram Isaac Beltran Conde, Mexico City (MX); Marco Antonio Dominguez Aguilar, Mexico City (MX); Jaquelin Martinez Viramontes, Mexico City (MX); Aristeo Estrada Buendia, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 397 days.

(21) Appl. No.: 14/563,234

(22) Filed: Dec. 8, 2014

(65) Prior Publication Data

US 2015/0089861 A1    Apr. 2, 2015

Related U.S. Application Data

(62) Division of application No. 13/151,573, filed on Jun. 2, 2011, now Pat. No. 10,035,757.

(30) Foreign Application Priority Data

Jun. 3, 2010 (MX) .................... MX/a/2010/006074

(51) Int. Cl.
*C07C 227/10*    (2006.01)
*C07C 227/16*    (2006.01)
(Continued)

(52) U.S. Cl.
CPC .......... *C07C 227/16* (2013.01); *C07C 227/10* (2013.01); *C07C 227/26* (2013.01);
(Continued)

(58) Field of Classification Search
CPC .......... C08L 1/12; C08L 1/221; C08L 1/2222; C08K 5/17; C08K 5/175; C08K 5/19; C07C 227/10; C07C 227/16; C07C 227/26
See application file for complete search history.

(56) References Cited

U.S. PATENT DOCUMENTS 2,195,974 A * 4/1940 Reppe ................. C07D 215/06
                                                    106/277
2,468,012 A    4/1949 Isbell
(Continued)

FOREIGN PATENT DOCUMENTS

EP    0353116    1/1990
EP    0526251    2/1993
(Continued)

*Primary Examiner* — Ellen M McAvoy
*Assistant Examiner* — Ming Cheung Po
(74) *Attorney, Agent, or Firm* — Dickinson Wright PLLC

(57) ABSTRACT

N-alkyl, N-alkenyl, N-cycloalkyl, N-aryl amino or imino propionic acids with an alkyl chain ranging from 6 to 18 carbons, or alkenyl chain from 8 to 30 carbons, are obtained from a reaction process in the absence of solvent at a temperature range from 30 to 180° C. and a time of 1 to 10 hours at atmospheric pressure. Formulations composed of N-alkyl or N-alkenyl or N-cycloalkyl or N-aryl amino or imino propionic acids, polyethers derived from propylene oxide or ethylene oxide or copolymer thereof and a solvent consisting of aromatic compounds such as toluene or xylene, diesel or gasoline or alcohols such as isopropanol and ethanol, or mixtures thereof, are obtained inhibit ferrous metal corrosion of pipelines and storage tanks and transport crude oil and liquid fuels. A method inhibiting corrosion of (Continued)

ferrous metals adds an effective amount of the corrosion inhibitor to a petroleum based material such as crude oil and liquid fuels such as gasoline, diesel fuel, and aviation fuel.

24 Claims, 1 Drawing Sheet

(51) Int. Cl.
| | |
|---|---|
| C07C 227/26 | (2006.01) |
| C07C 229/16 | (2006.01) |
| C23F 11/14 | (2006.01) |
| C10L 1/222 | (2006.01) |
| C10L 1/223 | (2006.01) |
| C10L 10/04 | (2006.01) |
| C07C 229/12 | (2006.01) |
| C07C 229/24 | (2006.01) |
| C09K 15/20 | (2006.01) |
| C10L 1/14 | (2006.01) |
| C10L 1/16 | (2006.01) |
| C10L 1/182 | (2006.01) |
| C10L 1/198 | (2006.01) |

(52) U.S. Cl.
CPC .......... *C07C 229/12* (2013.01); *C07C 229/16* (2013.01); *C07C 229/24* (2013.01); *C09K 15/20* (2013.01); *C10L 1/223* (2013.01); *C10L 1/2222* (2013.01); *C10L 10/04* (2013.01); *C23F 11/143* (2013.01); *C10L 1/143* (2013.01); *C10L 1/1608* (2013.01); *C10L 1/1616* (2013.01); *C10L 1/1824* (2013.01); *C10L 1/1985* (2013.01); *C10L 2200/0259* (2013.01); *C10L 2200/043* (2013.01); *C10L 2200/0423* (2013.01); *C10L 2200/0446* (2013.01); *C10L 2230/14* (2013.01); *C10L 2270/023* (2013.01); *C10L 2270/026* (2013.01); *C10L 2270/04* (2013.01); *C10L 2270/10* (2013.01); *C10L 2300/20* (2013.01)

(56) References Cited

U.S. PATENT DOCUMENTS

| | | | |
|---|---|---|---|
| 2,816,911 | A | 12/1957 | Aelony |
| 3,418,092 | A | 12/1968 | Andress et al. |
| 3,629,104 | A | 12/1971 | Maddox, Jr. |
| 4,214,876 | A | 7/1980 | Garth et al. |
| 4,450,137 | A | 5/1984 | Thompson et al. |
| 4,509,951 | A | 4/1985 | Knapp |
| 4,511,366 | A | 4/1985 | Burrows et al. |
| 4,709,089 | A * | 11/1987 | Shimizu ................ C07C 51/487 562/460 |
| 4,737,159 | A | 4/1988 | Phillips |
| 4,814,394 | A * | 3/1989 | Barthold .................. C08G 8/36 516/183 |
| 4,841,394 | A * | 6/1989 | Tomizawa ........... G11B 17/032 360/96.51 |
| 4,968,321 | A | 11/1990 | Sung et al. |
| 5,062,992 | A | 11/1991 | McCullough |
| 5,415,805 | A | 5/1995 | Brown et al. |
| 5,518,511 | A | 5/1996 | Russell et al. |
| 5,785,895 | A | 7/1998 | Martin et al. |
| 5,922,909 | A * | 7/1999 | Joffre .................... C07C 227/06 562/553 |

FOREIGN PATENT DOCUMENTS

| | | | | |
|---|---|---|---|---|
| EP | 1359206 | A1 * | 11/2003 | ............. C09K 8/524 |
| EP | 1359206 | A1 * | 11/2003 | ............. C09K 8/524 |

* cited by examiner

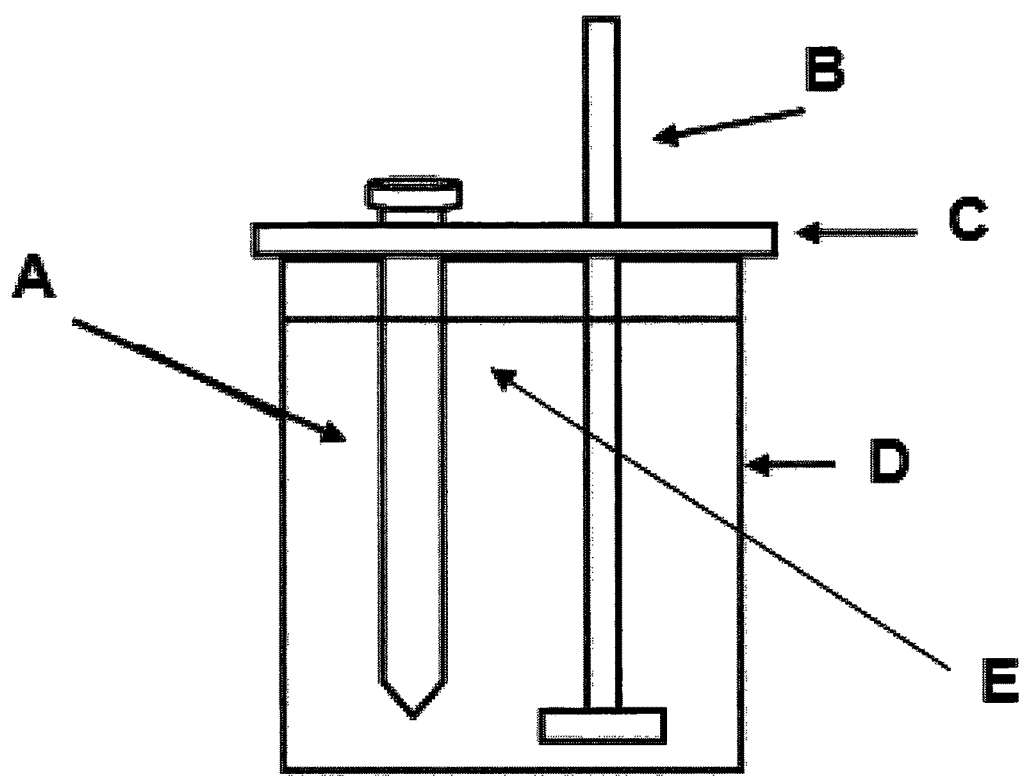

AMINO AND IMINO PROPIONIC ACIDS, PROCESS OF PREPARATION AND USE

CROSS-REFERENCE TO RELATED APPLICATIONS

This application is a divisional application of Ser. No. 13/151,573, filed Jun. 2, 2011, which claims the benefit under 35 U.S.C. § 119 of Mexican Patent Application No. MX/a/2010/006074, filed Jun. 3, 2010, which are hereby incorporated by reference in their entirety.

FIELD OF THE INVENTION

This invention is related to the development of a selective process for obtaining N-alkyl or N-alkenyl or N-cycloalkyl or N-aryl amino or imino propionic acids and its application in the development of corrosion inhibiting multifunctional compositions and formulations that protect and prevent the corrosion of ferrous metal in contact with crude oil with high concentration of hydrogen sulfide and liquid fuels as primary fuel without desulfurization, gasoline with low sulfur, gasoline from alkylation unit, jet fuel, methyl tertbutyl ether and diesel by the presence of acidic pollutants, sulfur compounds and water, and exposed to oxygen environments.

The corrosion inhibiting composition can be used in liquids fuels made from alcohols such as methanol, ethanol and propanol or gasoline-alcohol mixtures.

BACKGROUND OF THE INVENTION

The pipelines are commonly used for transportation of crude oils, usually used steel pipes of different diameters for this purpose.

Because the terrain features that are installed the pipelines, as well as fluids that are managed, it is necessary to protect materials of construction of the pipelines, both external and internal surfaces. With regard to internal corrosion, it is usually caused by contaminants in the crude oil, such as hydrogen sulfide, carbon dioxide, organic acids, water, minerals, suspended solids, asphaltenes, paraffins and microorganisms. Common ways to mitigate the damages include mechanical cleaning and the use of different chemicals such as corrosion inhibitors, scale inhibitors, biocides and dispersants.

The main damage caused by internal corrosion is uniform wear of the material, mainly due to the formation of iron sulphides and chlorides.

Globally and in México, there is a tendency of increasing the production of heavy crude oils, which generally have a higher content of pollutants.

Corrosion taking place in environments exposed to liquid fuels is a function directly related to the concentration of organic acids, organosulfur compounds, emulsified water and oxygen-rich environment. All of these factors together determine how aggressive this system can be.

Because of this, the global trend in the area of chemicals is the development of corrosion inhibitors with a greater degree of versatility to be able to control the corrosion levels despite significant increases in contaminants in the oil and fuel oil, which makes them more aggressive.

Most corrosion inhibitors used in the oil industry are organic compounds. The composition and chemical structure of the inhibitor significantly depend on the environment to which it will be immersed, is how they have the means in which the majority is water composition in which the organic phase is higher.

A variety of organic and inorganic compounds have been used to control corrosion in different aggressive media. Thus for packages employing aqueous based organic phosphonates, while for environments where the presence of hydrocarbons predominantly inhibitor use film base amino compounds, alcohols and imidazolinic compounds is a common practice.

Film corrosion inhibitors are usually composed of two parts: A polar electron-rich to be able to adhere to a metal surface through a coordination bond and a hydrophobic part that can be efficiently repel contaminants in the aggressive medium.

It is very important that the corrosion inhibiting composition does not emulsify water due to problems such as corrosion in pipelines and storage tanks or equipment failures and internal combustion engines.

Prior processes for obtaining N-alkyl or N-alkenyl or N-aryl beta-amino or imino propionic acids include:

U.S. Pat. No. 2,195,974 (Process for the production of new amino-carboxylic acid) discloses the development of new compounds such as N-alkyl or N-alkenyl or N-aryl beta-amino or imino propionic acids are produced from alkyl or alkenyl or aromatic amines and acrylic acid with water as a solvent with or without alkali metal bases.

U.S. Pat. No. 2,468,012 (beta-amino propionates) discloses the process of obtaining N-alkyl beta amino propionic acids produced from alkyl amines and esters of acrylic acid in the absence of solvent and subsequent neutralization with a alkali metal base.

U.S. Pat. No. 2,816,911 (Process of preparing N-alkyl-beta-alanine) discloses the process of obtaining N-alkyl beta amino propionic esters, which are produced from alkyl amines and esters of acrylic or methacrylic acid, in the absence of solvent, in a temperature range from 50 to 120° C. and subsequent neutralization with an alkali metal base.

U.S. Pat. No. 5,922,909 (Process for the selective control of amphoteric, zwitterionic compositions) discloses the process of obtaining N-alkyl or N-alkenyl or N-aryl beta-amino or imino propionic acids produced from alkyl or alkenyl or aromatic amines with beta-unsaturated acids in the presence of water in a pH range of 4.0 to 7.0, controlled by the addition of alkali metal bases or organic and subsequent neutralization with acid.

The use of corrosion inhibitors for ferrous metals in the transport and storage of liquid fuels include:

U.S. Pat. No. 4,214,876 (corrosion inhibiting composition) discloses the development of a formulation of the corrosion inhibition for ferrous metals exposed to hydrocarbon fuels made from 75 to 95% of an unsaturated aliphatic carboxylic acid of 16 to 18 carbons and 5 to 25% mono-alkenyl succinic acid with a chain from 8 to 18 carbons, and their use as a solvent hydrocarbon compounds.

U.S. Pat. No. 4,509,951 (Corrosion Inhibitor for alcohol-based fuels and gasoline-alcohol mixtures) discloses the development of a formulation of the corrosion inhibition for ferrous metals exposed to liquid motor fuels based on alcohol-gasoline blends alcohol consisting of aliphatic carboxylic acid polyunsaturated 18-carbon, and the reaction product of a polyamine with an alkenyl mono-unsaturated aliphatic carboxylic acid of 18 carbons or alkenyl succinic anhydride from 8 to 30 carbons.

U.S. Pat. No. 4,511,366 (Liquid fuels and concentrates containing corrosion inhibitors) discloses the development of a formulation of the corrosion inhibition for ferrous metals exposed to liquid alcohol-based fuel or gasoline-alcohol mixtures consisting of aliphatic carboxylic acid poly-unsaturated 16 to 18 carbons and a polyamine alkenyl.

U.S. Pat. No. 4,737,159 (Corrosion inhibitor for liquid fuels) discloses the development of a formulation of the corrosion inhibition for ferrous metals exposed to liquid hydrocarbon fuels made from 35 to 70% by weight of a monoalkylene succinic acid with a chain ranging from 8 to 18 carbons and 30 to 65% of aliphatic or cycloaliphatic amine containing from 2 to 12 carbons and solvents and aromatic hydrocarbon compounds alcohols of 1 to 4 carbons.

The use of corrosion inhibitors for ferrous metals used in the processing of crude oil include:

U.S. Pat. No. 3,629,104 discloses the obtaining of organic acid salts of basic compounds derived from 1-aminoalkyl-2-alkyl imidazolines and their use as corrosion inhibitors for ferrous metals in acidic characteristic of the oil industry. The efficiency of corrosion inhibition of these compounds was evaluated by gravimetric techniques.

U.S. Pat. No. 4,450,137 discloses a composition characterized by the presence of a mercaptan or polymercaptan group, an amido group or polyamide, and the use of this composition as a corrosion inhibitor for acid media.

U.S. Pat. No. 5,062,992 discloses a corrosion inhibiting formulation for oil and water systems, wherein the formulation is resistant to sludge formation and tends to stabilize oil in water. The corrosion inhibitor includes an imidazoline dissolved in an aromatic solvent, a 2-hydroxy alkyl carboxylic acid and glycol. The imidazoline is preferably prepared from the reaction of a long chain fatty acid and a polyamine in a molar ratio of 1.5:1.

EP 526,251, A1 discloses the production of corrosion inhibitors from the reaction of compounds 1-aminoalkyl base 2-alkyl imidazolines with acids or unsaturated organic esters.

U.S. Pat. No. 5,415,805 discloses a composition and method for inhibiting corrosion of ferrous metals that are in contact with aqueous systems containing sulfur compounds. Composition comprises an aqueous solution of an alcohol, an organic acid, a fatty imidazoline, an ethoxylated fatty diamine and an aqueous solution of compound of molybdenum.

U.S. Pat. No. 5,785,895 discloses a method for inhibiting corrosion in aqueous media. The method involves incorporating into the medium an amount of corrosion inhibitor sufficient to inhibit corrosion. The corrosion inhibitor comprises an N-ethoxy-2-imidazoline. The N-ethoxy substituent is comprised of one to thirty ethoxy units and the substituent at the position 2 can be a polyunsaturated fatty chain formed from six to thirty carbon atoms. If the medium is fresh, the inhibitor also be constituted of a phosphorus ester derived from a oxyethylated alcohol soluble in water.

SUMMARY OF THE INVENTION

The present invention is directed to the use of compounds based on N-alkyl, N-alkenyl, N-cycloalkyl, N-aryl amino, imino propionic acids, or mixtures thereof, as corrosion inhibitors of ferrous metals in contact with hydrocarbon fuels and crude oil. Surprisingly, the present invention obtains N-alkyl, N-alkenyl, N-aryl beta-amino or imino propionic acids from a reaction of alkyl or alkenyl or aromatic or cycloalkyl amines with alpha-beta unsaturated carboxylic acid in the absence of solvent. Additionally, the process of the present invention performs the reaction in the absence of a base derived from alkali metals or having an organic origin, and is conducted in a temperature range of 50° C. to 180° C. Purification of the beta-amino or imino acid can be performed through extraction of unreacted amines with hydrocarbon solvents like hexane.

The present invention is directed to a corrosion inhibiting composition and to a corrosion inhibiting amino or imino acid as corrosion inhibitors. The corrosion inhibiting amino or imino acid is an N-alkyl, N-cycloalkyl, N-alkenyl, N-aryl amine or imino propionic acid of structural formula:

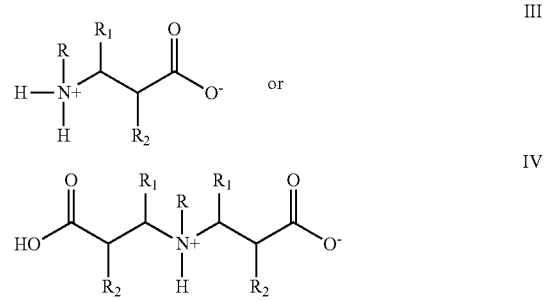

where R is a linear or branched alkyl or alkenyl chain having 1 to 30 carbon atoms or acylic alkyl or aryl group containing 5 to 12 carbon atoms, $R_1$ is a radical represented by —H or —$CH_3$ and $R_2$ is —H. The corrosion inhibiting composition can include a mixture of the propionic acid and dipropionic acid.

The corrosion inhibiting composition contains an effective amount of the amino or imino acid of the invention to inhibit corrosion of ferrous metals. The corrosion inhibiting composition is particularly effective in inhibiting corrosion of pipelines and containers that contain petroleum based materials and liquids such as crude oil and petroleum fuels such as gasoline, diesel and aviation fuel, jet fuel and alcohols. The corrosion inhibiting composition can be included in an amount of 1 to 200 ppm based on the weight of the petroleum based material.

The corrosion inhibiting formulation in one embodiment contains a mixture of the amino or imino acid of the invention, a polyether obtained from polypropylene oxide or ethylene oxide or copolymers thereof and a solvent. The solvent can be an aromatic solvent such as toluene or xylene, alcohols such as methanol, ethanol and isopropanol, gasoline, diesel and mixtures thereof. The formulation can contain 10% to 90% by weight of the amino or imino acid of the invention, and 10% to 90% by weight of a solvent. The formulation can contain the polyether in an amount of up to 40% by volume based on the weight of the formulation. The polyether can be included in an amount of 0-40% by weight. The polyether can have a weight average molecular weight of about 100-3000 g/mol.

The corrosion inhibiting formulation can include a mixture of a propionic acid of formula III and a dipropanoic acid of formula IV. In one embodiment, the formula contains a mixture of a dipropanoic acid and a propanoic acid in a molar ratio of 90:10 by weight.

The invention is further directed to a method of inhibiting corrosion of pipelines and containers containing crude oil of flammable liquids by adding an effective amount of a compound of formula III and/or formula IV to inhibit corrosion of ferrous metals. The crude oil can have a high concentration of hydrogen sulfide. The liquid fuel can be gasoline such as gasoline that has not been desulfurized, gasoline obtained by an alkylation process, jet fuel, methyltertiary butyl ether (MTBE), diesel fuel or alcohol.

The various features of the invention are also attained by providing a petroleum based material or liquid such as crude oil or fuel containing an effective amount of a corrosion inhibiting agent where the corrosion inhibiting agent is an amino or imino propionic acid of formula III or formula IV and mixtures thereof. The corrosion inhibiting agent can be present in an amount of 1 to 200 ppm. Flammable liquids can contain the corrosion inhibiting agent in an amount of 5 to 25 ppm. Crude oil containing high amounts of hydrogen sulfide can include about 25 to about 100 ppm of the corrosion inhibiting agent.

BRIEF DESCRIPTION OF THE DRAWINGS

FIG. 1 shows the testing device used by the NACE TM-0172 method to determine the effectiveness of corrosion inhibiting compounds of the present invention.

DETAILED DESCRIPTION OF THE INVENTION

The present invention relates to the application and process for obtaining a corrosion inhibiting zwitterionic composition that prevents and reduces the corrosion caused by acidic compounds, air pollutants, sulfur compounds, water and environments exposed to oxygen in ferrous metal pipelines and liquid storage tanks for primary hydrocarbon fuels such as gasoline without desulfurizing, gasoline with low sulfur, gasoline from alkylation unit, jet fuel, methyl tertbutyl ether and diesel fuel and alcohol compounds such as methanol, ethanol or propanol, or mixtures of gasoline-alcohol. The corrosion inhibiting composition may be composed of 2 components. The first component can vary from 0 to 100% by weight of an N-alkyl-amino propionic acid with an alkyl chain ranging from 6 to 18 carbons, or an N-alkenyl-amino propionic acid with an alkenyl chain from 8 to 30 carbons, or N-cycloalkyl-amino propionic acid or N-aryl-amino propionic acid. The second component can vary from 0 to 100% of an N-alkyl imino propionic acid with an alkyl chain ranging from 6 to 18 carbons, or an N-alkenyl-imino propionic acid with an alkenyl chain from 8 to 30 carbons, or N-cycloalkyl-imino propionic acid or N-aryl imino-propionic acid. The corrosion inhibiting composition can be formulated using it as an asset in a concentration range that can range from 10 to 90% by weight of a solvent containing 0.1 to 40% by weight of a polyether derived from propylene oxide or ethylene oxide or copolymer of average molecular weight in the range of 100-3000 g/mol, 10 to 90% by weight of a solvent consisting of aromatic compounds such as toluene or xylene, diesel or gasoline or alcohols such as isopropanol and ethanol, or mixtures thereof.

The composition consisting of N-alkyl or N-alkenyl or N-cycloalkyl or N-aryl amino and/or imino propionic acids are obtained from a selective process that occurs in the absence of a solvent at atmospheric pressure by reacting an alkyl or alkenyl or cycloalkyl or aromatic amine with an alpha-beta unsaturated carboxylic acid, at a temperature range of 50° C. to 180° C. and a reaction time of between 1 and 10 hours. Purification of beta-amino or imino acid can be made through extraction of unreacted amines with hydrocarbon solvents like hexane.

All components that are part of the corrosion inhibiting composition were characterized by $^1H$ NMR and $^{13}C$ and infrared spectroscopy.

The efficiency of corrosion inhibition for ferrous metals was evaluated through the NACE TM-0172 method for liquid fuels as primary fuel, gasoline with low sulfur content, gasoline from alkylation unit, jet fuel, methyl tertbutyl ether, diesel, low molecular weight alcohols such as ethanol and gasoline-alcohol mixtures in the presence of a high water content and the method NACE TM-1D-182 for ferrous metals exposed to environments characteristic of crude oil containing a high salt content and saturation of hydrogen sulfide at pH 4.

Therefore, a feature of the present invention is to provide a composition containing an active compound derived from the N-alkyl or N-alkenyl or N-cycloalkyl or N-aryl amino or imino propionic acids, a polyether derived from ethylene oxide, propylene oxide or copolymers thereof and an aromatic hydrocarbon solvent, low molecular weight alcohols or a combination thereof. The composition outperforms the existing corrosion inhibitors because it has the multifunctionality of inhibiting corrosion of ferrous metals in contact with crude oil and liquid fuels.

Another additional contribution of the present invention is to provide a process for manufacturing the active compound N-alkyl or N-alkenyl or N-cycloalkyl or N-aryl amino or imino propionic acids.

Preparation Process of Selective Inhibitory Composition of Corrosion.

The compounds of the present invention are obtained according the synthesis scheme (1).

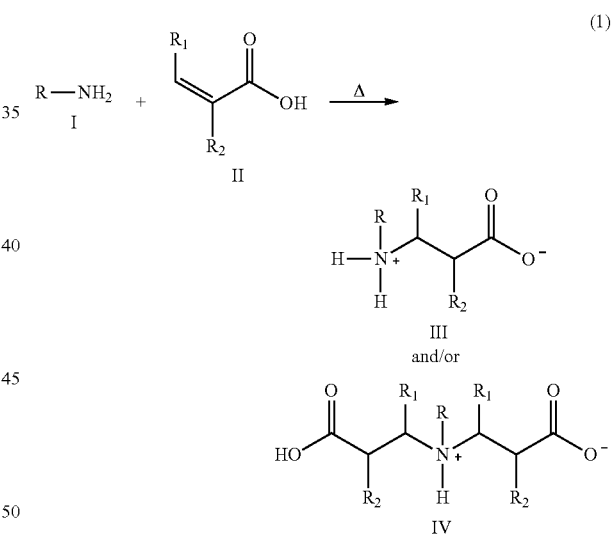

where R, $R_1$ and $R_2$ are as defined above.

The production process consists of the following:

In the absence of solvent, a linear or branched alkyl amine (I) selected from the group consisting of oleylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine or a linear or branched alkenyl amine selected the group consisting of oleylamine, linoleylamine, eurocylamine, behenylamine and taloylamine or cycloalkyl amine such as cyclohexylamine, or aromatic amine such as aniline and benzylamine, with an alpha, beta unsaturated carboxylic acid or diacid (II) selected from: acrylic acid and methacrylic acid, in a range of temperatures ranging from 50 to 180° C. and for 1 to 10 hours, and preferably 2 to 8 hours.

Purification of beta-amino or imino acid can be made through extraction of unreacted amines with hydrocarbon solvents like hexane.

The amine-acid molar ratio ranges from 0.5 to 3.0 and 3.0 to 0.5, preferably in the range of 1.0 to 2.0 and 2.0 to 1.0. In additional embodiments, the reaction is carried out at a temperature of 30° C. to 180° C., typically 50° C. to 180° C., and preferably 50° C. to 120° C. in the absence of a solvent and at atmospheric pressure. The resulting reaction product can be purified by extracting with a suitable solvent such as hexane.

The following examples will illustrate the process of obtaining selective corrosion inhibitory compositions of the present invention but not limit the scope thereof.

Example 1

Process for obtaining the corrosion inhibiting composition comprising 3,3'-(octadec-9-enylazanediyl)dipropanoic acid (1).

In a three-necked balloon flask of 500 ml equipped with a magnetic stirrer, a dropping funnel, a thermometer and a condenser were added 50 g (0.187 mol) of oleylamine at a temperature of 40° C. with vigorous stirring was slowly added to 26.9 g (0.37 mol) of acrylic acid. The reaction is exothermic and the temperature under these conditions rises gradually to 90° C. The reaction mixture was stirred under these conditions for 1 hour and a half and then increased to 100° C., thus obtaining 76 g of compound corrosion inhibitor consisting of a mixture of two products with a molar ratio of 90% for the 3,3'-(octadec-9-enylazanediyl)dipropanoic acid and 10% of the 3-(octadec-9-enylamino)propanoic acid, as a very viscous pale yellow, the spectroscopic features are: FTIR (cm$^{-1}$): 2921, 2854, 1723, 1645, 1572, 1461, 1348, 1291, 1211, 1115, 962, 830. $^1$H NMR (CDCl$_3$), 200 MHz, δ (ppm): 5.28, 3.20, 2.91, 2.61, 1.94, 1.20, 0.82. $^{13}$C NMR (CDCl$_3$), 50 MHz, δ (ppm): 175.4, 174.6, 129.8, 129.5, 52.3, 49.7, 47.3, 32.5, 31.8, 29.6, 29.2, 27.1, 22.5 and 14.0.

Example 2

Process for obtaining the corrosion inhibiting composition consisting of 3-(octadec-9-enylamino)propanoic acid (2).

In a three-necked balloon flask of 500 ml equipped with a magnetic stirrer, a dropping funnel, a thermometer and a condenser were added 50 g (0.187 mol) of oleylamine at a temperature of 40° C. with vigorous stirring slowly added 13.48 g (0.187 mol) of acrylic acid. The reaction is exothermic and the temperature under these conditions rises gradually to 90° C. The reaction mixture was stirred under these conditions for 2 hours and then increased to 100° C. Purification of amino propionic acid was performed using an extraction of the amine did not react with hexane, thus obtaining 63 g of corrosion inhibitor compound with a yield of 92% as a very viscous pale yellow, features spectroscopy are: FTIR (cm$^{-1}$): 2921, 2854, 1642, 1575, 1463, 1349, 1288, 1209, 1116, 963, 833. $^1$H NMR (CDCl$_3$), 200 MHz, δ (ppm): 5.31, 3.02, 2.73, 2.47, 1.98, 1.25, 0.85. $^{13}$C NMR (CDCl$_3$), 50 MHz, δ (ppm): 176.8, 129.9, 129.7, 47.5, 44.8, 40.8, 31.8, 29.7, 29.5, 29.2, 27.2, 22.6 and 14.1.

Example 3

Process for obtaining the corrosion inhibiting composition comprising 3,3'-(octadecylazanediyl)dipropanoic acid (3).

In a three-necked balloon flask of 500 ml equipped with a magnetic stirrer, a dropping funnel, a thermometer and a condenser were added 50 g (0.186 mol) of octadecylamino and a temperature of 45° C. with vigorous stirring was slowly added 26.8 g (0.37 mol) of acrylic acid. The reaction is exothermic and the temperature under these conditions rises gradually to 90° C., maintaining the temperature for about an hour and then increases to 140° C. The reaction mixture was stirred under these conditions for 4 hours, thus obtaining the compound 76 g corrosion inhibitor consisting of a mixture of two products with a molar ratio of 90% for 3,3'-(octadecylazanediyl)dipropanoic acid and 10% of the 3-(octadecylamino)propanoic acid as a very viscous pale yellow, the spectroscopic features are: FTIR (cm$^{-1}$): 2921, 2854, 1721, 1655, 1574, 1460, 1345, 1292, 1210, 1116, 965, 831. $^1$H NMR (CDCl$_3$), 200 MHz, δ (ppm): 3.19, 2.92, 2.63, 1.21, 0.81. $^{13}$C NMR (CDCl$_3$), 50 MHz, δ (ppm): 175.4, 174.6, 52.1, 49.5, 47.6, 32.2, 31.9, 29.5, 29.1, 27.3, 22.1 and 13.9.

Example 4

Process for obtaining the corrosion inhibiting composition comprising 3-(dodecylamino)propanoic acid (4).

In a flask ball three-necked 500 ml equipped with a magnetic stirrer, a dropping funnel, a thermometer and a condenser were added 50 g (0.27 mol) of dodecylamine and a temperature of 40° C. with vigorous stirring were added very slowly 38.88 g (0.54 mol) of acrylic acid. The reaction is exothermic and the temperature under these conditions is rising gradually to 90-100° C., leaving the stable temperature for about an hour and a half, and then increasing the temperature to 160° C. The reaction mixture was stirred under these conditions for 8 hours, thus obtaining 79 g corrosion inhibitor compound with a yield of 90% as a very viscous clear orange, the spectroscopic features are: FTIR (cm$^{-1}$): 2921, 2854, 1725, 1653, 1581, 1463, 1345, 1292, 1210, 1118, 955, 831. $^1$H NMR (CDCl$_3$), 200 MHz, δ (ppm): 3.21, 2.95, 2.65, 1.22, 0.85. $^{13}$C NMR (CDCl$_3$), 50 MHz, δ (ppm): 174.7, 52.2, 49.6, 47.5, 32.1, 31.8, 29.4, 29.3, 27.2, 22.3 and 13.9.

Example 5

Process for obtaining the corrosion inhibiting composition comprising 3,3'-(octylazanediyl)dipropanoic acid (5).

In a three-necked 500 ml ball flask equipped with a magnetic stirrer, a dropping funnel, a thermometer and a condenser were added 50 g (0.39 mol) of octylamine at a temperature of 30° C. with vigorous stirring was added slowly 55.8 g (0.77 mol) of acrylic acid. The reaction is exothermic and the temperature under these conditions is rising gradually to 90-100° C., maintaining the temperature for two hours and then increase the temperature to 150° C. The reaction mixture was stirred under these conditions for 10 hours, thus obtaining 79 g corrosion inhibitor compound with a yield of 75% as a very viscous pale yellow, the spectroscopic features are: FTIR (cm$^{-1}$): 2922, 2851, 1726, 1658, 1567, 1455, 1345, 1285, 1216, 1120, 968, 831. $^1$H NMR (CDCl$_3$), 200 MHz, δ (ppm): 3.23, 2.94, 2.61, 1.19, 0.79. $^{13}$C NMR (CDCl$_3$), 50 MHz, δ (ppm): 174.6, 52.5, 49.1, 47.8, 32.1, 31.7, 29.2, 29.1, 27.1, 22.4 and 13.9.

Example 6

Process for obtaining the corrosion inhibiting composition consisting of 3-(dodecylamino)propanoic acid (6).

In a three-necked balloon flask of 500 ml equipped with a magnetic stirrer, a dropping funnel, a thermometer and a condenser were added 90.8 g (0.49 mol) of dodecylamine and a temperature of 30° C. with vigorous stirring was added slowly 32.4 g (0.45 mol) of acrylic acid. The reaction is exothermic and the temperature under these conditions is rising gradually to 90-100° C., maintaining the temperature for two hours and then increase the temperature to 150° C. The reaction mixture was stirred under these conditions for 12 hours. Purification of amino beta was performed using an extraction of the amine that did not react with hexane, thus obtaining the compound 109 g corrosion inhibitor with a yield of 92% as a white solid, the spectroscopic features are: FTIR (cm$^{-1}$): 2926, 2851, 1652, 1566, 1462, 1343, 1295, 1209, 1116, 969, 833. $^1$H NMR (CDCl$_3$), 200 MHz, δ (ppm): 3.03, 2.71, 2.45, 1.93, 1.25, 0.85. $^{13}$C NMR (CDCl$_3$), 50 MHz, δ (ppm): 176.8, 47.3, 44.5, 40.7, 31.1, 29.5, 29.3, 29.2, 27.1, 22.5 and 14.0.

Preparation of Corrosion Inhibitory Formulations

The following examples will illustrate the formulations object of the present invention but not limit the scope thereof.

Example 7

Formulation 1, which consisted of 50% by weight of the corrosion inhibiting composition comprising a mixture of 3,3'-(octadec-9 enylazanediyl)dipropanoic acid and 10% of the 3-(octadec-9-enylamino)propanoic acid with a molar ratio of 90 and 10% respectively, and 50% by weight of a mixture of isomers of xylene.

Example 8

Formulation 2, which consisted of 50% by weight of the corrosion inhibiting composition consisting of 3-(octadec-9-enylamino)propanoic acid and 50% by weight of a mixture of isomers of xylene.

Example 9

Formulation 3, which consisted of 50% by weight of the corrosion inhibiting composition comprising a mixture of 3,3'-(octadecylazanediyl)dipropanoic acid and 3-(octadecylamino) propanoic acid with a molar ratio of 90 and 10% respectively, and 50% by weight of a mixture of isomers of xylene.

Example 10

Formulation 4, which consisted of 50% by weight of the corrosion inhibiting composition comprising 3-(dodecylamino)propanoic acid and 50% by weight of a mixture of isomers of xylene.

Example 11

Formulation 5, which consisted of 50% by weight of the corrosion inhibiting composition comprising 3,3'-(octylazanediyl)dipropanoic acid and 25% by weight of a mixture of isomers of xylene and 25% ethanol.

Example 12

Formulation 6, which consisted of 50% by weight of the corrosion inhibiting composition consisting of 3-(dodecylamino)propanoic acid and 50% by weight of a mixture of isomers of xylene.

Example 13

Formulation 7, which consisted of 22% of the corrosion inhibiting composition comprising 3,3'-(octadec-9 enylazanediyl)dipropanoic acid, 28% by weight of a polyether of average molecular weight of 1100 g/mol derived from propylene oxide and ethylene oxide and 50% by weight of a mixture of isomers of xylene.

Example 14

Formulation 8, which consisted of 22% of the corrosion inhibiting composition comprising a mixture of 3,3'-(octadec-9 enylazanediyl)dipropanoic acid and 10% of the 3-(octadec-9-enylamino)propanoic acid with molar ratio of 90 and 10% respectively, 28% by weight of a polyether of average molecular weight of 1100 g/mol derived from propylene oxide and ethylene oxide and 50% by weight of a mixture of isomers of xylene.

Performance Testing

Determination of the Efficiency of Corrosion Inhibition by the Method NACE TM-0172.

Test Description

Test Method NACE TM-0172 is to determine the corrosive properties of gasoline, jet fuel and distillate fuels that found in pipelines and storage tanks. Also includes information on metal specimen preparations, equipment and a system for ranking the test samples with corrosion inhibitor. The testing device is shown in FIG. 1 where the device includes a glass container D containing a test sample A, a digitally controlled stirrer B, a cover C made of polytetrafluoroethylene and a hydrocarbon water mixture E.

Testing Equipment and Apparatus

The apparatuses consist of:
A temperature measuring device.
One bath. Should be used a thermally controlled bath of mineral oil capable of maintaining a temperature in the test sample 38±1° C. The bathroom must have a cover with holes to accommodate the test glass and the temperature measuring device.

The test device used by the NACE TM-0172 method to determine the efficiency of corrosion inhibition posed by gemini surfactants of the present invention, illustrated by FIG. 1, consists of a test specimen (A), a digitally controlled stirrer (B), a cover of poly (tetrafluoroethylene) (C), a glass (D), and hydrocarbon-water mixture (E).

The sample must be a steel yarn 81.0×12.7 mm, the steel shall conform to UNS* G10150 (Grade 1015), UNS G10180 (1018), UNS G10200 (1020) or UNS G10250 (1025) ASTM A108, used with a plastic handle of poly(tetrafluoroethylene) (PTFE).

(*Unified Numbering System).

Test Procedure

Add 300 ml of fuel to the test vessel and dispensed corrosion inhibitor to the desired concentration, the glass is placed in an oil bath at a temperature of 38±1° C. after 30 minutes of continuous stirring add 30 ml of distilled water, and agitation continued for three hours. Subsequently the sample is removed, and left to drain and washed with toluene or xylene followed by acetone.

Sample Qualification

The rating should be based solely on the portion of the sample that remained in the test fluid. The corrosion products formed during the test have had limited opportunity to darken, and all deposits of solids not removed by washing of toluene and acetone should be considered as products of corrosion. Marks on the circle can occur during polishing and should not be interpreted as corrosion, classification is based according to Table 1.

TABLE 1

| Qualification | Percentage of corroded surface |
|---|---|
| A | 0 |
| B++ | Less than 0.1 |
|  | (2 or 3 spots of no more than 1 mm in diameter). |
| B+ | Less than 5 |
| B | 5-25 |
| C | 25-50 |
| D | 50-75 |
| E | 75-100 |

Table 2 shows the results of Formulation 1 with a variety of liquid fuels.

TABLE 2

| Formulation | Concentration (ppm) | Test Medium (liquid fuel) | Qualification (NACE TM-0172) |
|---|---|---|---|
| Reference | 0 | All | E |
| 1 | 5 | Gasoline without desulfurization | A |
| 1 | 5 | Gasoline | A |
| 1 | 5 | Gasoline with low sulfur | A |
| 1 | 5 | Diesel | A |
| 1 | 5 | MTBE | A |
| 1 | 5 | Gasoline from alkylation unit | A |
| 1 | 5 | Gasoline with low sulfur/Ethanol (50:50) | A |

Table 3 shows the results of formulation 2 with a variety of liquid fuels.

TABLE 3

| Formulation | Concentration (ppm) | Test medium (liquid fuel) | Qualification (NACE TM-0172) |
|---|---|---|---|
| Reference | 0 | All | E |
| 2 | 5 | Gasoline without desulfurization | A |
| 2 | 5 | Gasoline | A |
| 2 | 5 | Gasoline with low sulfur | A |
| 2 | 5 | Diesel | A |
| 2 | 5 | MTBE | A |
| 2 | 5 | Gasoline from alkylation unit | A |
| 2 | 5 | Gasoline with low sulfur/Ethanol (50:50) | A |

Tables 4, 5 and 6 show the results of formulations 1, 2, 3, 4, 5 and 6 with gasoline at different concentrations.

TABLE 4

| Formulation | Concentration (ppm) | Qualification (NACE TM-0172) |
|---|---|---|
| Reference | 0 | E |
| 1 | 15 | A |
| 2 | 15 | A |
| 3 | 15 | A |
| 4 | 15 | B++ |
| 5 | 15 | C |
| 6 | 15 | A |

TABLE 5

| Formulation | Concentration (ppm) | Qualification (NACE TM-0172) |
|---|---|---|
| Reference | 0 | E |
| 1 | 25 | A |
| 2 | 25 | A |
| 3 | 25 | A |
| 4 | 25 | B++ |
| 5 | 25 | B |
| 6 | 25 | A |

TABLE 6

| Formulation | Concentration (ppm) | Qualification (NACE TM-0172) |
|---|---|---|
| Reference | 0 | E |
| 1 | 50 | A |
| 2 | 50 | A |
| 3 | 50 | A |
| 4 | 50 | A |
| 5 | 50 | A |
| 6 | 50 | A |

Table 7 shows the results of formulations 7 and 8 with gasoline at different concentrations.

TABLE 7

| Formulation | Concentration (ppm) | Qualification (NACE TM-0172) |
|---|---|---|
| Reference | 0 | E |
| 7 | 10 | A |
| 7 | 15 | A |
| 7 | 20 | A |
| 8 | 10 | A |
| 8 | 15 | A |
| 8 | 20 | A |

Determination of the Corrosion Inhibition Efficiency Through NACE 1 D-182 Method.

Gravimetric test is commonly called dynamic wheel (Wheel test) that simulates the corrosive environment characteristic of oil production, is a dynamic procedure developed for fluids (oil, water and inhibitor).

Testing Equipment and Reagents:
a) Evaluating dynamic for corrosion inhibitors with temperature controller, stirrer speed of 30 rpm and capacity for 52 bottles of 180 ml.
b) Bottles of 200 ml capacity.
c) Coupon SAE 1010 carbon steel, dimension 2.540×1.270× 0.025 cm (1"×0.5"×0.010").
d) Glassware for the preparation of a corrosive environment. This consist of a glass reactor of 2 liter, equipped with a cooling bath, mechanical stirrer, bubbler for gas (nitrogen and hydrogen sulfide), has an outlet connected to two traps in serie (the first with sodium hydroxide in pellet form and the second with another sodium hydroxide solution 20% in weight), so that hydrogen sulfide does not contaminate the environment.

e) Potentiometer for measuring pH.

The test conditions are shown in table 8.

TABLE 8

| Temperature | 70° C. |
|---|---|
| Aqueous medium | Synthetic brine with 600 ± 50 ppm de $H_2S$ |
| Test time | 46 hours |
| Organic medium | Kerosene |
| Volume ratio Synthetic brine/organic medium | 90/10 |
| Test volume | 180 ml |
| pH | 4 |
| Metals coupons | Steel SAE 1010 |

The composition of the brine is shown in Table 9.

TABLE 9

| Salts | Amount (g/l) |
|---|---|
| NaCl | 60.0 |
| $CaCl_2 \cdot H_2O$ | 6.0 |
| $MgCl_2 \cdot 6H_2O$ | 10.48 |
| $Na_2SO_4$ | 3.5 |

Results:

The difference in weight of the coupons before and after being exposed to corrosive liquid for 46 hours, is a direct indication of metal lost due to corrosion.

The efficiency of corrosion inhibition is obtained by comparing the reference coupon wear with the wear of the coupons with corrosion inhibitor at different concentrations, using the following formula (2):

Efficiency=$(Vo-V)/V \times 100$

Where:

Vo=Corrosion velocity of reference coupon (standard).

V=Corrosion velocity of coupon with corrosion inhibitor

Table 10 shows the results for formulations 1, 2 and 3 at different concentrations

TABLE 10

| Formulation | Concentration (ppm) | Corrosion velocity *(mpy's) | Efficiency (%) |
|---|---|---|---|
| Blanco | 0 | 32.9 | 0 |
| 1 | 10 | 2.5 | 91.6 |
| 1 | 25 | 2.8 | 91.4 |
| 1 | 50 | 2.0 | 93.8 |
| 2 | 10 | 2.8 | 91.4 |
| 2 | 25 | 2.9 | 90.9 |
| 2 | 50 | 2.8 | 91.4 |
| 3 | 10 | 4.09 | 90.9 |
| 3 | 25 | 2.7 | 91.9 |
| 3 | 50 | 2.6 | 91.8 |
| 6 | 10 | 2.4 | 92.1 |
| 6 | 25 | 2.8 | 91.4 |
| 6 | 50 | 1.9 | 94.0 |

*mpy's: thousandths of an inch per year

Table 11 shows the results for formulations 7 and 8 at different concentrations:

TABLE 11

| Formulation | Concentration (ppm) | Corrosion velocity *(mpy's) | Efficiency (%) |
|---|---|---|---|
| Blanco | 0 | 31.4 | 0 |
| 7 | 25 | 2.6 | 91.8 |
| 7 | 50 | 2.5 | 92.0 |
| 7 | 75 | 2.1 | 93.3 |
| 8 | 25 | 2.4 | 92.4 |
| 8 | 50 | 2.2 | 92.9 |
| 8 | 75 | 1.9 | 93.9 |

*mpy's: thousandths of an inch per year

Determination of the Efficiency of Corrosion Inhibition by Electrochemical Techniques.

Equipment Used:

A glass electrochemical cell, reference electrode, working electrode, counter electrode, pH meter, multimeter, potentiostat/galvanostat Autolab PGSTAT 30 71410 were provided. The preparation of the bitter brine of pH 4, and the dissolution of chemicals in isopropanol in order to prepare a solution of 1,000 ppm in 100 mL were obtained in a suitable container.

Test Procedure:

A specimen of carbon steel 1010 with an area of 0.5 $cm^2$ by grinding with #600 sandpaper. The bitter brine is the same as was used for the gravimetric technique. Polarization curves were generated linear open-circuit potential ±25 mV. When the test is obtained polarization curve, which is analyzed to determine the corresponding corrosion rate. To make a new experiment is necessary to perform the roughing electrode is placed in the cell and generate another curve. This procedure is repeated until there is a coincidence of at least two curves. The experiments were performed at room temperature with magnetic stirring and bitter brine adjusted to pH 4.0±1. The corrosion rate (mpy) is determined through manipulation of the curve using the program of the potentiostat.

Table 12 shows the results for formulations 1, 2, 3 and 4 at different concentrations:

TABLE 12

| Formulation | Concentration (ppm) | Corrosion velocity *(mpy's) | Efficiency (%) |
|---|---|---|---|
| Blanco | 0 | 72 | 0 |
| 1 | 25 | 18 | 75 |
| 1 | 50 | 12 | 83 |
| 2 | 25 | 21 | 71 |
| 2 | 50 | 18 | 75 |
| 3 | 25 | 16 | 78 |
| 3 | 50 | 12 | 83 |

*mpy's: thousandths of an inch per year

Determination of the Tendency to Emulsify Water by the Method ASTM D-1094.

This test method covers the determination of the presence of water miscible components of gasoline and jet fuel, and the effects of these components on the change of volume and hydrocarbon-water interface.

Test Procedure

The test steps are:

1. It is measured 20 mL of water at room temperature in the specimen and record the volume and add 80 mL of oil (jet fuel) and the inhibitor formulation dosed at different concentrations (10 ppm, 20 ppm) and cover the specimen.
2. Specimen is stirred for 2 minutes+/−5 seconds, with 2 or 3 strokes per second. Avoid twisting motions during agitation of the specimen.

3. Immediately, the specimen is placed on a vibration-free surface and leave the contents for 5 minutes.

4. Without lifting the specimen, are recorded scattered light observations:

a) The change in volume of the aqueous phase.

b) The appearance of the interface based on table 13.

c) The degree of separation of the two phases based on table 14

TABLE 13

| Qualification | Appearance |
|---|---|
| (1) | Complete absence of emulsions and/or precipitates at each stage or phase of the oil. |
| (2) | Same qualifying conditions (1), except for the presence of small bubbles of air or water in the hydrocarbon phase. |
| (3) | Emulsions and/or precipitates in each phase or hydrocarbon phase, and/or droplets in the aqueous phase or attached to the walls of the specimen, excluding the walls above the hydrocarbon phase. |

TABLE 14

| Qualification | Appearance |
|---|---|
| 1 | Clean and clear |
| 1b | Clear bubbles covering not more than 50% of the interface and free of fragmentation, thread or film at the interface. |
| 2 | Fragmentation, thread or film at the interface |
| 3 | Loose threads or thin cream, or both. |
| 4 | Threads narrow or thick cream, or both. |

Table 15 shows the results for formulations 7 and 8 at different concentrations:

TABLE 15

| Formulation | Concentration (ppm) | Qualification of phase separation | Qualification of interface |
|---|---|---|---|
| 7 | 10 | 1 | 1b |
| 7 | 15 | 2 | 1b |
| 8 | 10 | 1 | 1b |
| 8 | 15 | 2 | 1b |

As shown in table 15 the developed formulations 7 and 8 have efficiencies above 90% in tests of corrosion inhibition for hydrogen sulfide saturated environments and liquid fuels, and it does not emulsify.

While various embodiments have been chosen to illustrate the invention, it will become apparent that various changes and modifications can be made without departing from the scope of the appended claims.

What is claimed is:

1. A corrosion inhibiting composition including a corrosion inhibiting compound consisting of N-alkenyl amine or imino propionic acid of structural formula:

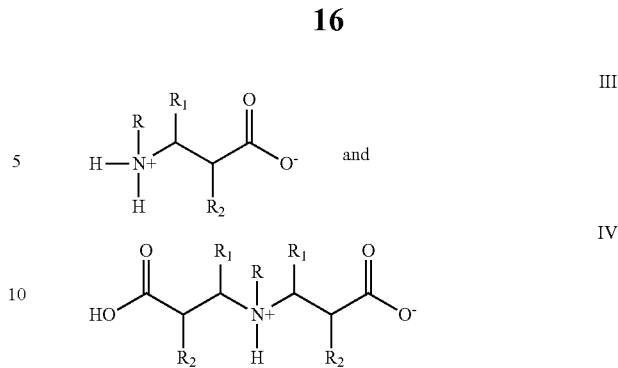

where R is a linear or branched alkenyl chain having 1 to 30 carbon atoms, R1 is a radical represented by —H or —CH3 and R2 is —H.

2. A composition adapted for inhibiting corrosion of ferrous metals, said composition containing at least one N-alkenyl amino or imino propionic acid, wherein said amino or imino propionic acids are produced by a reaction process in the absence of solvent, in the absence of a base, and at atmospheric pressure, said process comprising reacting an alkyl, alkenyl, cycloalkyl or aromatic amine of formula I with an alpha-beta unsaturated carboxylic acid of formula II according to the following synthesis scheme (3) in the absence of a solvent and in the absence of a base to obtain the compounds of formula III and/or IV

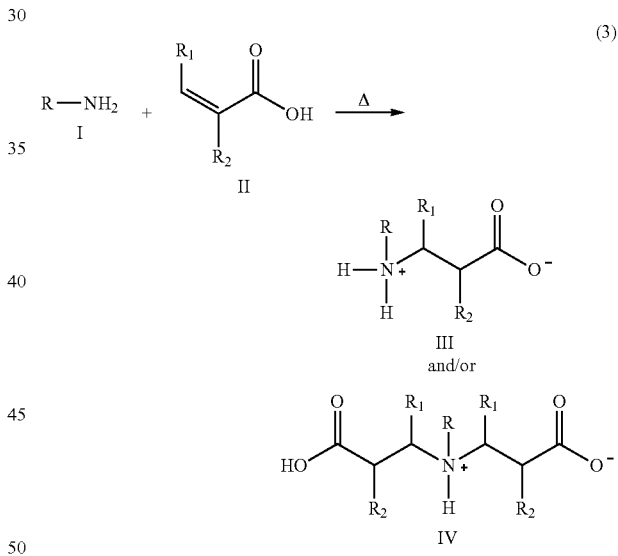

the reaction being carried out at a temperature range of 50 to 180° C. and a reaction time between 1 and 10 hours, where R is a linear or branched alkyl or alkylene group having 1 to 30 carbon atoms, R1 is H or —CH3 and R2 is H.

3. The composition according to claim 2, wherein the compound of formula II is an alpha-beta unsaturated carboxylic acid selected from the group consisting of acrylic acid and methacrylic acid.

4. The composition according to claim 2, wherein the compound II is acrylic acid.

5. The composition according to claim 2, wherein the amine-acid molar ratio is 0.5:3 to 3:0.5.

6. The composition according to claim 2, wherein the reaction is carried out at a temperature range of 30° C. to 180° C.

7. The process composition to claim 2, wherein the reaction time is between 1 and 10 hours.

8. The composition according to claim 2, wherein the resulting amino or imino propionic acids are purified by extracting with a hydrocarbon solvent.

9. The composition according to claim 8, where the hydrocarbon solvent is hexane.

10. A corrosion inhibiting formulation consisting essentially of:
   a) N-alkenyl amino or imino propionic acids having the formula

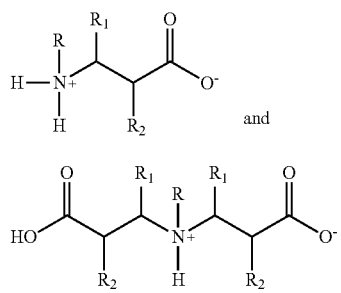

where R is an alkenyl chain having 1 to 30 carbon atoms, R1 is a radical represented by —H or —CH3 and R2 is —H;

b) a polyether derived from propylene oxide or ethylene oxide or copolymer thereof in an amount of not more than 40% by weight based on the weight of the amino or imino propionic acid, and
   c) a solvent consisting of aromatic compounds selected from the group consisting of toluene and xylene, and an alcohol selected from the group consisting of methanol, ethanol and isopropanol, gasoline, diesel, and mixtures thereof.

11. The corrosion inhibiting formulation according to claim 10, where the concentration of N-alkenyl amino or imino propionic acids is in the range of 10% to 90% by weight.

12. The corrosion inhibiting formulation according to claim 10, wherein the concentration of solvent used is in the range of 10% to 90% by weight based on the weight of the amine or imino propionic acid.

13. The corrosion inhibiting formulation according to claim 10, wherein the solvent is xylene.

14. The formulation of claim 10, wherein the weight average molecular weight polyether derived from propylene oxide or ethylene oxide or copolymer thereof is 100-3000 g/mol.

15. A corrosion inhibiting composition comprising:
   at least one component selected from the group consisting of gasoline, jet fuel, MTBE, diesel fuel and alcohol; and
   a corrosion inhibiting compound consisting of a compound of formula III or formula IV in an amount of 1 to 200 ppm to inhibit corrosion of ferrous metals in contact with said composition, wherein said compound is an N-alkenyl amino or imino propionic acid of structural formula:

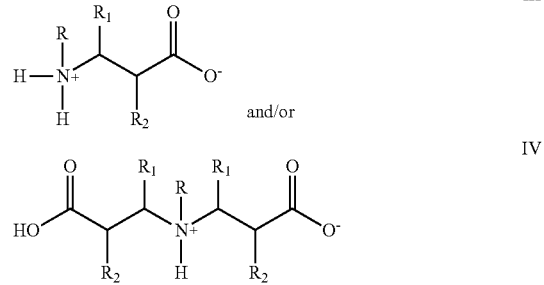

where R is an alkenyl chain having 1 to 30 carbon atoms, $R_1$ is a radical represented by —H or —$CH_3$ and $R_2$ is H; and a polyether derived from propylene oxide or ethylene oxide.

16. The composition of claim 15, wherein
   the compound of formula III or formula IV is present in an amount of 5 to 25 ppm.

17. The composition of claim 15, wherein
   the compound of formula III or formula IV is present in an amount of 25 to 100 ppm.

18. The composition of claim 15, including a mixture of said compound of formula III and compound of formula IV.

19. The composition of claim 18, wherein
   said compound of formula IV and compound of formula III are present in a ratio of 90:10 by weight.

20. The composition of claim 19, wherein
   said compound of formula IV is 3,3'-(octadec-9 enylazanediyl) dipropionic acid and said compound of formula III is 3-(octadec-9-enylamino) propionic acid.

21. The composition of claim 15, wherein
   said compound of formula III is selected from the group consisting of an N-alkenyl-amino propionic acid having an alkenyl group with 8-30 carbon atoms.

22. The composition of claim 15, wherein
   said compound of formula IV and is selected from the group consisting of N-alkenyl-imino propionic acid having an alkyl or alkenyl chain of 8-30 carbons.

23. The composition of claim 15, wherein
   said at least one corrosion inhibiting compound is selected from the group consisting of an N-alkenyl-amino propionic acid having an alkenyl group with 8-30 carbon atoms; and
   at least one selected from the group consisting of an N-alkenyl-imino propionic acid having an alkenyl group with 8-30 carbon atoms.

24. The composition of claim 15, wherein said amino or imino propionic acid is selected from the group consisting of 3,3'-(octadec-9 enylazanediyl)dipropanoic acid, 3-(octadec-9-enylamino)propanoic acid, 3,3'-(octadec-9 enylazanediyl) dipropanoic acid and 10% of the 3-(octadec-9-enylamino) propanoic acid, 3-(dodecylamino)propanoic acid, and mixtures thereof.

* * * * *